United States Patent
Wattiaux

(10) Patent No.: US 9,955,673 B1
(45) Date of Patent: May 1, 2018

(54) MILK UREA-N YIELD (MUNY) AS A NUTRITIONAL AND ENVIRONMENTAL MANAGEMENT TOOL FOR THE DAIRY INDUSTRY

(71) Applicant: Wisconsin Alumni Research Foundation, Madison, WI (US)

(72) Inventor: Michel Andre Wattiaux, Madison, WI (US)

(73) Assignee: Wisconsin Alumni Research Foundation, Madison, WI (US)

(*) Notice: Subject to any disclaimer, the term of this patent is extended or adjusted under 35 U.S.C. 154(b) by 1 day.

(21) Appl. No.: 14/794,187

(22) Filed: Jul. 8, 2015

Related U.S. Application Data

(60) Provisional application No. 62/021,950, filed on Jul. 8, 2014.

(51) Int. Cl.
| | |
|---|---|
| *G01N 33/48* | (2006.01) |
| *A01K 29/00* | (2006.01) |
| *G01N 33/483* | (2006.01) |
| *G06G 7/48* | (2006.01) |

(52) U.S. Cl.
CPC ......... *A01K 29/005* (2013.01); *G01N 33/483* (2013.01)

(58) Field of Classification Search
None
See application file for complete search history.

*Primary Examiner* — Eric S Dejong
(74) *Attorney, Agent, or Firm* — Boyle Fredrickson, SC

(57) ABSTRACT

The present disclosure provides methods and systems for optimizing a cost efficiency or a nitrogen-use efficiency (NUE) for a feeding regimen of a herd of interest of milk-producing animals, for monitoring a urinary urea-N excretion (UUNE) for a herd of interest of milk-producing animals, and for monitoring a NUE for a herd of interest of milk-producing animals. The methods include use of a milk urea-N yield (MUNY) value or a ratio of MUNY to a protein yield (PY) in milk produced by the herd of interest.

10 Claims, 5 Drawing Sheets

US 9,955,673 B1

MILK UREA-N YIELD (MUNY) AS A NUTRITIONAL AND ENVIRONMENTAL MANAGEMENT TOOL FOR THE DAIRY INDUSTRY

CROSS-REFERENCE TO RELATED APPLICATION

This application claims priority to U.S. Provisional Patent Application No. 62/021,950, filed Jul. 8, 2014, the entire contents of which are incorporated herein in their entirety by reference.

STATEMENT REGARDING FEDERALLY SPONSORED RESEARCH OR DEVELOPMENT

This invention was made with government support under 2009-51160-19789 awarded by the USDA/NIFA. The government has certain rights in the invention.

FIELD OF THE INVENTION

The present disclosure relates to methods and systems for increasing efficiency in feeding herds of milk-producing animals. More particularly, systems and methods are provided for improving a cost efficiency or nitrogen-use efficiency (NUE) for a feeding regimen of a herd of milk-producing animals, and monitoring a NUE or urinary urea-N excretion (UUNE) for a herd of milk-producing animals.

BACKGROUND OF THE INVENTION

Nitrogen in the livestock diet arises primarily from crude protein (CP) in feed. While needed for proper health and milk production, too much nitrogen in the diet results in an excess of nitrogen excreted into the environment. This excessive nitrogen excretion comes at a financial cost to the farmer who may be spending too much money on high protein feed or overfeeding, as well as an environmental cost. The dairy industry has explored ways of reducing excess dietary nitrogen by monitoring levels of excreted nitrogen in the form of urea in the milk and urine, and adjusting CP levels in the feed accordingly. However, farmers are concerned that by dropping CP levels too low, cows will consume less feed (sources of supplemental protein are typically very palatable) and as a result milk production will suffer. Currently, there is not a good method of optimizing efficient use of nitrogen in dairy herds.

In controlled experiments, the concentration of urea-N in milk, commonly referred to as milk urea-N (MUN), has been highly correlated with dietary crude protein (CP) level, nitrogen-use efficiency (NUE), and urinary urea-N excretion (UUNE). However, under field conditions, variations due to non-nutritional factors (e.g., sampling type, frequency of milking, milk production) and lack of information about the N intake on the day that data are sampled have lessened the value of MUN as a management tool.

Previous efforts have failed to recognize the importance of the ratio of milk urea-N yield (MUNY) and protein yield (PY) in economically feeding cattle without causing deleterious effects to the environment by the excretion of nitrogen. Moreover, existing methods are incapable of providing feedback to a user that would enable the adjustment of feeding practices within a day of measuring and interpreting data.

Accordingly, a need exists for methods that do not suffer from the mentioned shortcomings.

SUMMARY OF THE INVENTION

The present disclosure is based on the inventor's recent discovery of milk urea-N yield (MUNY) values as predictors of urinary urea-nitrogen excretion (UUNE), and the use of MUNY per unit of protein yield (PY) values as an indicator of nitrogen use efficiency (NUE). The inventors' strategy facilitates a means of optimizing the economics of animal feeding while reducing the negative impact on the environment of excess nitrogen secretion using an algorithm and values that are already being measured in the vast majority of dairy herds. In addition, the methods and systems described herein enable adjustment of feeding practices within a day of measuring and interpreting data.

Accordingly, in a first aspect, the disclosure is directed to methods of optimizing a cost efficiency or a nitrogen-use efficiency (NUE) for a feeding regimen of a herd of interest of milk-producing animals. The method may comprise one or more of the following steps: a) accessibly storing an observation data set comprising an amount of milk produced by the herd of interest on an observation date ($MP_O$), a concentration of urea-N in milk produced by the herd of interest on the observation date ($MUN_O$), a protein yield in milk produced by the herd of interest on the observation date ($PY_O$), and a percent dietary crude protein in feedstock consumed by the herd of interest on the observation date or a date one to seven days before the observation date ($CP_O$) on a dry matter basis; b) calculating a ratio ($MUNY_O/PY_O$) of a milk urea-N yield by the herd of interest on the observation date ($MUNY_O$) to the $PY_O$, wherein the $MUNY_O$ is the $MUN_O$ divided by the $MP^O$; c) defining an optimal target ratio ($MUNY_T/PY_T$); and d) generating a report recommending use of a single feedstock or a mixture of feedstock expected to alter the $CP_O$ upward if the $MUNY_O/PY_O$ is less than the $MUNY_T/PY_T$ or recommending use of a single feedstock or a mixture of feedstock expected to alter the $CP_O$ downward if the $MUNY_O/PY_O$ is greater than the $MUNY_T/PY_T$.

Given that $PY_O$ is likely to respond to changes in dietary feedstock composition, the methods may further include repeating steps a), b), and d) substituting a new observation date for the observation date, wherein the new observation date is one or more days after the observation date.

The methods may further include accessibly storing a historical data set including an amount of milk produced by the herd of interest, one or more comparable herds, or a combination thereof on one or more dates within a historical time window ($MP_H$), a concentration of urea-N in milk produced by the herd of interest, the one or more comparable herds, or a combination thereof on the one or more dates within the historical time window ($MUN_H$), and a protein yield in milk produced by the herd of interest, the one or more comparable herds, or a combination thereof on the one or more dates within the historical time window ($PY_H$), and a percent dietary crude protein in feedstock consumed by the herd of interest, the one or more comparable herds, or a combination thereof on the one or more dates or a date one to seven days before the one or more dates within the historical time window ($CP_H$) on a dry matter basis; and using the historical data set in step c). In certain aspects, step c) includes a regression analysis of the historical data set representative of a legitimate expectation for farms located in distinct locales, reflecting regional differences within the United States or within the boundaries of any country worldwide.

The methods further include adding the observation data set to the historical data set and including the observation date in the historical time window; and repeating steps a), b), and d) substituting a new observation date for the observation date, wherein the new observation date is one or more days after the observation date.

In certain aspects, $PY_O$ is between about 500 grams per day and about 2000 grams per day.

In certain aspects, the $MUNY_O$ is between about 1.0 grams per day and about 10.0 grams per day.

The methods further include measuring the $MP_O$, the $MUN_O$, the $PY_O$, and the $CP_O$ to form the observation data set.

The methods further include feeding the herd of interest on one or more days after the observation date with a feedstock having a percent dietary crude protein that is equal to the $CP_O$ if the $MUNY_O/PY_O$ is less than the $MUNY_T/PY_T$ or feeding the herd of interest on one or more days after the observation date with a feedstock having a percent dietary crude protein that is greater than or less than the $CP_O$ if the $MUNY_O/PY_O$ is greater than the $MUNY_T/PY_T$.

In a second and related aspect, the disclosure provides a method of monitoring a urinary urea-N yield for a herd of interest of milk-producing animals (UUNE). Such a method includes one or more of the following steps: a') measuring an amount of milk produced by the herd of interest (MP) and a concentration of urea-N in milk produced by the herd of interest (MUN); b') estimating the UUNE by multiplying a milk urea-N yield for the herd of interest (MUNY) by a UUNE conversion factor, wherein the MUNY is the MUN divided by the MP; and c') generating a report including the UUNE.

In certain aspects, the UUNE has g/d for units, the MUNY has mg/d for units, and the UUNE conversion factor is about 26.8 g/mg.

In certain aspects, the herd of interest has a UUNE between about 40 grams per day and about 200 grams per day.

In a third and related aspect, the disclosure provides a method of monitoring a nitrogen use efficiency for a herd of interest of milk-producing animals (NUE). Such a method includes one or more of the following steps: a") measuring an amount of milk produced by the herd of interest (MP), a concentration of urea-N in milk produced by the herd of interest (MUN), and a protein yield in milk produced by the herd of interest (PY); b") estimating the NUE by dividing a ratio (MUNY/PY) of a milk urea-N yield for the herd of interest (MUNY) and the PY by a NUE conversion factor, wherein the MUNY is the MUN divided by the MP; and c") generating a report including the NUE.

In certain aspects, the methods do not directly measure any properties of the urine of the herd of interest of milk-producing animals.

In certain aspects, the milk-producing animals are dairy cattle.

As can be appreciated, the disclosure encompasses the use of any of the methods or systems described herein for altering a feeding strategy for a herd of interest of milk-producing animals.

Other objects, features and advantages of the present invention will become apparent after review of the specification, claims and drawings. The detailed description and examples enhance the understanding of the invention, but are not intended to limit the scope of the appended claims.

DETAILED DESCRIPTION OF THE INVENTION

Figure 1:
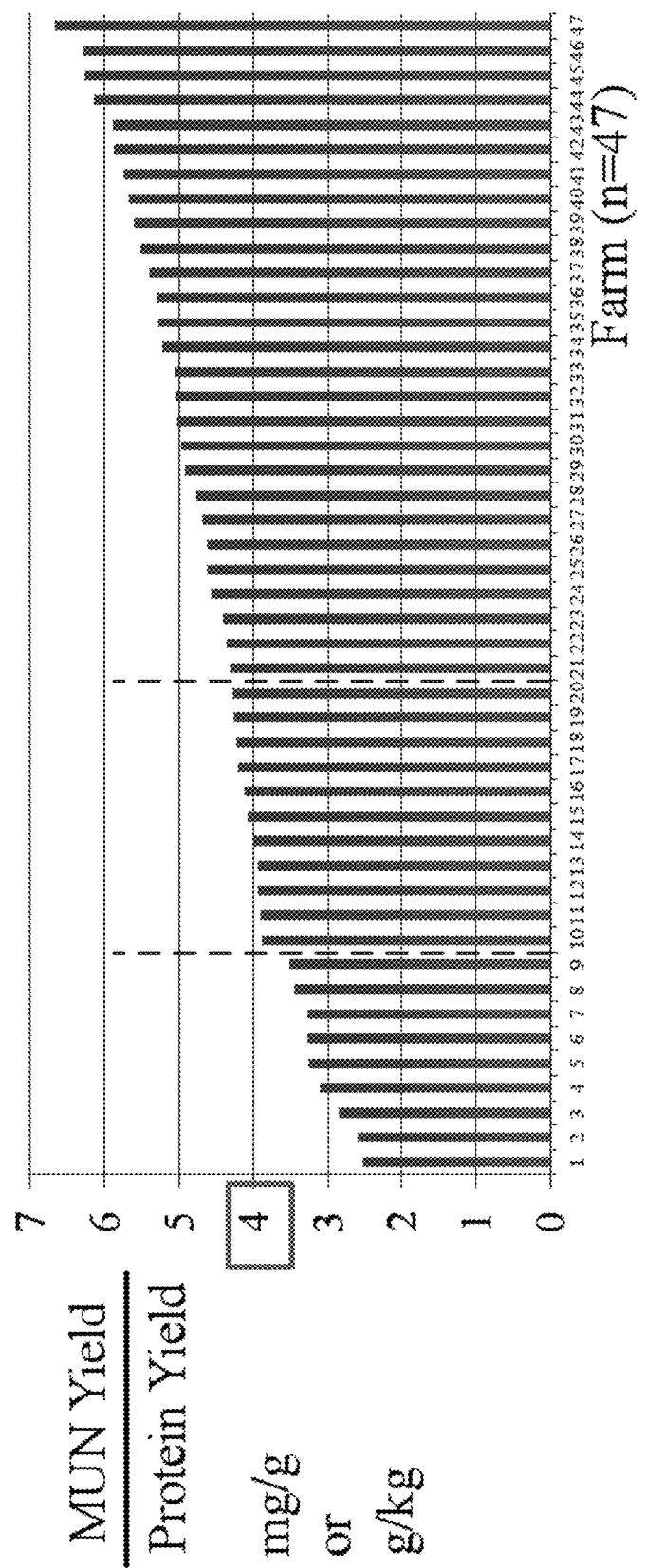
FIG. 1 is a histogaram showing a ratio of milk urea-N yield versus protein yield for 47 herds, as described in Example 1.

Before the present materials and methods are described, it is understood that this invention is not limited to the particular methodology, protocols, materials, and reagents described, as these may vary. It is also to be understood that the terminology used herein is for the purpose of describing particular embodiments only, and is not intended to limit the scope of the present invention, which will be limited only by the appended claims.

It must be noted that as used herein and in the appended claims, the singular forms "a", "an", and "the" include plural reference unless the context clearly dictates otherwise. As well, the terms "a" (or "an"), "one or more" and "at least one" can be used interchangeably herein. It is also to be noted that the terms "comprising", "including", and "having" can be used interchangeably.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described. All publications and patents specifically mentioned herein are incorporated by reference for all purposes including describing and disclosing the chemicals, animals, instruments, statistical analyses, and methodologies which are reported in the publications which might be used in connection with the invention. All references cited in this specification are to be taken as indicative of the level of skill in the art. Nothing herein is to be construed as an admission that the invention is not entitled to antedate such disclosure by virtue of prior invention.

The practice of the present invention will employ, unless otherwise indicated, conventional techniques of zoology, agriscience, organic chemistry, analytical chemistry, molecular biology, and microbiology, which are within the skill of the art. Such techniques are explained fully in the literature.

This disclosure provides methods and systems for optimizing a cost efficiency or a nitrogen-use efficiency (NUE) for a feeding regimen of a herd of interest of milk-producing animals, monitoring a urinary urea-N excretion (UUNE) for a herd of interest of milk-producing animals, and monitoring a NUE for a herd of interest of milk-producing animals.

The disclosure described herein is based on a discovery that a ratio of milk urea-N yield (MUNY) and protein yield (PY) is strongly correlated to NUE and MUNY is strongly correlated to UUNE.

Based on these observations and studies, it was discovered that MUNY and MUNY/PY can be used to monitor feeding efficiency in cattle.

The concentration of urea-N in milk (MUN) is a measure of the amount of urea-N in milk per unit volume. MUN is a standard measurement at a typical dairy facility.

The amount of milk produced (MP) is a measure of the total amount of milk produced by a herd over a given time period, typically a day. MP is a standard measurement at a typical dairy facility.

The milk-urea-N yield (MUNY) is calculated by dividing the MUN by the MP. Accordingly, MUNY can be calculated by data taken by standard measurements at a typical dairy facility.

Protein yield (PY) in milk is a measure of the amount of protein in the milk produced by a herd over a given time period, typically a day. PY is a standard measurement at a typical dairy facility.

A percent dietary crude protein (CP) is a measure of what percent, on a dry matter basis, of the feedstock for cattle is made of crude protein. CP can be calculated or estimated based on the known composition of the feedstock by techniques known to those having ordinary skill in the art.

Subscript 'O' indicates a measurement that is part of the observation data set, subscript 'H' indicates a measurement that is part of the historical data set, and subscript 'T' indicates an optimal target value.

This disclosure provides a method of optimizing a cost efficiency or a NUE for a feeding regimen of a herd of interest of milk producing animals. The methods may comprise one or more of the following steps: accessibly storing an observation data set comprising an amount of milk produced by the herd of interest on an observation date ($MP_O$), a concentration of urea-N in milk produced by the herd of interest on the observation date ($MUN_O$), a protein yield in milk produced by the herd of interest on the observation date ($PY_O$), and a percent dietary crude protein in feedstock consumed by the herd of interest on the observation date or a date one to seven days before the observation date ($CP_O$) on a dry matter basis; calculating a ratio ($MUNY_O/PY_O$) of a milk urea-N yield by the herd of interest on the observation date ($MUNY_O$) to the $PY_O$, wherein the $MUNY_O$ is the $MUN_O$ divided by the $MP_O$; defining an optimal target ratio ($MUNY_T/PY_T$); and generating a report recommending use of a single feedstock or a mixture of feedstock expected to alter the $CP_O$ upward if the $MUNY_O/PY_O$ is less than the $MUNY_T/PY_T$ or recommending use of a single feedstock or a mixture of feedstock expected to alter the $CP_O$ downward if the $MUNY_O/PY_O$ is greater than the $MUNY_T/PY_T$.

In certain aspects, the methods may comprise generating a report recommending use of a single feedstock or a mixture of feedstock expected to alter the $CP_O$ upward if the $MUNY_O/PY_O$ is less than about 99%, about 95%, about 90%, about 75%, or about 50% of the $MUNY_T/PY_T$ or recommending use of a single feedstock or a mixture of feedstock expected to alter the $CP_O$ downward if the $MUNY_O/PY_O$ is greater than about 101%, about 105%, about 110%, about 125%, or about 150% than the $MUNY_T/PY_T$.

In certain aspects, the methods further comprise feeding the herd of interest on one or more days after the observation date with a feedstock or a mixture of feedstock expected to alter the $CP_O$ upward if the $MUNY_O/PY_O$ is less than the $MUNY_T/PY_T$ or feeding the herd of interest on one or more days after the observation date with a feedstock or mixture of feedstock expected to alter the $CP_O$ downward if the $MUNY_O/PY_O$ is greater than the $MUNY_T/PY_T$.

In certain aspects, the methods may comprise feeding the herd of interest on one or more days after the observation date with a single feedstock or a mixture of feedstock expected to alter the $CP_O$ upward if the $MUNY_O/PY_O$ is less than about 99%, about 95%, about 90%, about 75%, or about 50% of the $MUNY_T/PY_T$ or feeding the herd of interest on one or more days after the observation date a single feedstock or a mixture of feedstock expected to alter the $CP_O$ downward if the $MUNY_O/PY_O$ is greater than about 101%, about 105%, about 110%, about 125%, or about 150% of than the $MUNY_T/PY_T$.

Accessibly storing an observation data set can be achieved by methods known to those having ordinary skill in the art. For example, an observation data set could be accessibly stored on a hard drive, on a disk drive, in a computing cloud, or the like.

Defining an optimal target ratio ($MUNY_T/PY_T$) may involve setting a point above which and below which the $MUNY_O/PY_O$ causes a recommended change or a change in feeding behavior. In some aspects, defining a $MUNY_T/PY_T$ may involve setting an optimal NUE target and converting the optimal NUE target into a $MUNY_T/PY_T$. In certain aspects, defining a $MUNY_T/PY_T$ may involve altering $CP_O$ in a direction that increases the $PY_O$ over the course of more than one day until the $PY_O$ no longer increases or increases by less than about 1%, about 5%, about 10%, or about 25% in response to the altered $CP_O$. In certain aspects, the optimal target value is herd-specific.

Feeding the herd on one or more days after the observation date is an action step taken in response to the recommendation in the report.

The methods may also comprise repeating one or more of the method steps substituting a new observation date for the observation date, wherein the new observation date is one or more days after the observation date. A person having ordinary skill in the art should appreciate that this method can be performed on a daily basis, thereby allowing fine-tuning of the feeding practices for cattle.

The methods may also comprise accessibly storing a historical data set comprising an amount of milk produced by the herd of interest, one or more comparable herds, or a combination thereof on one or more dates within a historical time window ($MP_H$), a concentration of urea-N in milk produced by the herd of interest, the one or more comparable herds, or a combination thereof on the one or more dates within the historical time window ($MUN_H$), and a protein yield in milk produced by the herd of interest, the one or more comparable herds, or a combination thereof on the one or more dates within the historical time window ($PY_H$), and a percent dietary crude protein in feedstock consumed by the herd of interest, the one or more comparable herds, or a combination thereof on the one or more dates or a date one to seven days before the one or more dates within the historical time window ($CP_H$) on a dry matter basis. Accessibly storing a historical data set can be achieved by methods known to those having ordinary skill in the art. For example, a historical data set could be stored on a hard drive, on a disk drive, in a computing cloud, or the like.

As used herein, a "comparable herd" shall refer to a herd that is metabolically similar to the herd of interest in terms of one or more of the following comparison variables: breed of animal, region, feed composition, altitude, soil composition, precipitation, average seasonal temperature, average sun exposure, and other properties known by those having ordinary skill in the art to impact the metabolic properties of a herd. To determine if a second herd is metabolically similar to the herd of interest, a historical data set for the herd of interest and a historical data set for the second herd may be subjected to a regression analysis using one or more of the comparison variables.

In certain aspects comprising a historical data set, the methods may comprise defining an optimal target ratio ($MUNY_T/PY_T$) using the historical data set. In some aspects, defining an optimal target ratio ($MUNY_T/PY_T$) using the historical data set may comprise a regression analysis of the historical data set. In some aspects, the methods further comprise adding the observation data set to the historical data set and including the observation date in the historical time window; and repeating one or more steps substituting a new observation date for the observation date, wherein the new observation date is one or more days after the observation date.

In certain aspects, the historical data set is comprised entirely of data for the herd of interest. In these aspects, the historical data set serves as an internal standard for the herd of interest. The internal standard may be a MUNY/PY ratio that optimizes NUE for the herd of interest and may be calculated via a regression analysis on the historical data set. It should be appreciated that the internal standard can be used with the herd of interest or with a herd for which the herd of interest is a comparable herd.

In certain aspects, the historical data set is comprised entirely of data for comparable herds. In these aspects, the historical data set serves as an external standard for the herd of interest. The external standard may be a locally agreed upon acceptable MUNY/PY ratio reflecting what can be expected in terms of NUE across distinct farms of a region or a country. It should be appreciated that the external standard can be used with any herd for which the herds making up the historical data set are comparable herds.

In certain aspects, the historical data set is comprised of data for the herd of interest and data for comparable herds. In these aspects, the historical data set serves as a hybrid external/internal standard for the herd of interest. It should be appreciated that the hybrid external/internal standard can be used with the herd of interest or with a herd for which the herd of interest and the herds making up the historical data set are comparable herds.

In certain aspects, $PY_O$ may be between about 250 g/d and about 3000 g/d, between about 500 g/d and about 2000 g/d, or between about 600 g/d and about 1300 g/d.

In certain aspects, the $MUNY_O$ may be between about 0.5 g/d and about 15.0 g/d, between about 1.0 g/d and about 10.0 g/d, or between about 1.25 g/d and about 9.0 g/d.

This disclosure also provides a method of monitoring a urinary urea-N excretion (UUNE) for a herd of milk-producing animals, the method comprising one or more of the following steps: measuring an amount of milk produced by the herd (MP) and a concentration of urea-N in milk produced by the herd (MUN); estimating the UUNE by multiplying a milk urea-N yield for the herd (MUNY) by a UUNE conversion factor, wherein the MUNY is the MUN divided by the MP; and generating a report including the UUNE.

A person having ordinary skill in the art should appreciate that this method allows an estimate of UUNE to be produced without actually monitoring the urine of a herd of cattle. In certain aspects, the methods do not directly measure any properties of the urine of the herd of milk-producing animals. Since milk from dairy cattle is monitored more regularly and more rigorously than urine from dairy cattle, these methods afford the ability to estimate and monitor nitrogen output in urine with regularly-measured properties of the milk that is produced.

In certain aspects, the UUNE has g/d for units, the MUNY has mg/d for units, and the UUNE conversion factor may be about 26.8 g/mg. The UUNE conversion factor may vary depending on regional and national conditions for the herd of interest. The UUNE conversion factor for a region of interest can be determined using a regression analysis of historical data sets for herds within the region of interest. A UUNE conversion factor may be adjusted based on new data. As the genetic makeup of cattle changes, either by natural or artificial selection, the metabolic properties of cattle may change as a result and the UUNE conversion factor may be updated by performing a regression analysis on data representing the new metabolic properties of cattle.

In certain aspects, the herd may comprise a UUNE between about 40 g/d and about 240 g/d or between about 50 g/d and about 125 g/d.

This disclosure also provides methods of monitoring a NUE for a herd of milk-producing animals, the method comprising one or more of the following steps: measuring an amount of milk produced by the herd (MP), a concentration of urea-N in milk produced by the herd (MUN), and a protein yield in milk produced by the herd (PY); estimating the NUE by dividing a ratio (MUNY/PY) of a milk urea-N yield for the herd (MUNY) and the PY by a NUE conversion factor, wherein the MUNY is the MUN divided by the MP; and generating a report including the NUE.

This disclosure also provides methods of optimizing the economic benefits for a herd of milk producing animals by utilizing a difference of income and feed cost. The difference of income to feed cost can be calculated with economic data specific to a region of interest (for example, the Midwest of the United States). The income can be calculated using the price of milk in the region of interest, the amount of milk, yield of fat, yield of lactose, and yield of protein. The feed cost can be calculated as the cost of each ingredient (optionally with units of dollars per pound) weighted for the particular ingredient's proportion in the diet. In certain aspects, an ideal ratio of income to feed cost can be maintained by monitoring a MUNY or a MUNY/PY of a herd. In certain aspects, the target $MUNY_T$ or the $MUNY_T/PY_T$ can be the respective MUNY or MUNY/PY value that produces the maximum difference of income to feed cost.

In certain aspects, the MUNY/PY ratio can be calculated using a ratio of MUN and a concentration of protein in milk, provided that the differences in am and pm values are taken into consideration.

It should be appreciated that wherever the MUNY/PY ratio is described herein, its inverse, the PY/MUNY ratio can be substituted in ways that would be clear to those having ordinary skill in the art. Where MUNY/PY ratio is explicitly described, PY/MUNY ratio is also contemplated. In certain aspects, the methods and systems described herein can utilize the MUNY in place of the MUNY/PY ratio.

In certain aspects, the methods do not directly measure any properties of the urine of the herd of milk-producing animals.

In certain aspects, the milk-producing animals are dairy cattle.

Any of the methods as described herein can be deployed as part of a system, wherein the system comprises a means for executing the method steps (such as a computer or a portable computing device, such as a tablet or smart phone) and a herd data collection system (such as a system for collecting DHI data).

Example 1

A Dairy Herd Improvement (DHI) data set (AgSource-CRI) spanning 9 years, including 529 DHI herds, and including approximately 1.5 million test-day MUN records was subjected to a regression analysis. No linear relationship (P=0.08) was discernible between PY and herd-level MUN. However, the relationship between PY (g/d) and MUNY (mg/d) was described by the following equation:

$$PY=0.173+4.19\times MUNY \quad (1)$$

($r^2$=0.995, P<0.001) for PY in the range of 600 to 1300 g/d.

In the DHI data set, 47 herds had data that allowed the MUNY to be calculated in the same fashion as it was in the nutritional study. In those 47 herds, the MUNY/PY averaged 4.6±0.01 mg/g and values for individual herds ranged from 2.5 mg/g to 6.7 mg/g. Referring to FIG. 1, a histogram showing the MUNY/PY for those 47 herds is shown. By defining a target MUNY/PY (i.e., a $MUNY_T/PY_T$) of 4.0 mg/g±0.25 mg/g [PLEASE CONFIRM THAT THIS IS THE RANGE.], it was shown that 9 herds had a MUNY/PY that was too low (those to the left of both vertical dashed lines), 11 herds had a MUNY/PY that was ideal (those between the vertical dashed lines), and 27 herds had a MUNY/PY that was too high (those to the right of both vertical dashed lines). Those herds having a MUNY/PY that was too low had dietary CP that was too low, sub-optical PY, and UUNE that was too minimal. Those herds having a MUNY/PY that was too high had dietary CP that was too high, sub-optimal protein yield, and excessive UUNE.

Example 2

A 128-cow nutritional study was conducted. In the nutritional study, MUNY was calculated as an average morning and evening MUN weighted by milk production at each milking. The relationship between UUNE (g/d) and MUNY (mg/d) was described by the following equation:

$$UUNE=26.8\times MUNY \quad (2)$$

($r^2$=0.991, P<0.001) for UUNE in the range of 40 to 240 g/d.

Additionally, in the nutritional study, mid-to-late lactation cows were fed diets of 11.8%, 13.1%, 14.6%, and 16.2% crude protein (dry matter basis) over four consecutive days and the MUNY/PY (mean±standard error) was 1.1±0.3 mg/g, 2.2±0.3 mg/g, 3.6±0.5 mg/g, and 4.3±0.3 mg/g on respective days. Over the course of the four consecutive days, the NUE decreased linearly (P<0.01), thus showing an inverse linear relationship between NUE and MUNY/PY.

Over the course of twelve weeks, mid-to-late lactation cows were split into four equal groups and respectively fed diets of 11.9%, 13.4%, 14.4%, and 16.2% crude protein (dry matter basis). The MUNY/PY (mean±standard error) was 1.2±0.3 mg/g for the cows fed the 11.9% diet, 2.2±0.3 mg/g for the cows fed the 13.4% diet, 2.8±0.4 mg/g for the cows fed the 14.4% diet, and 3.6±0.5 mg/g for the cows fed the 16.2% diet.

Example 3

Data was gathered from 23 different studies and those studies collectively involved 80 different dietary treatments. The studies were as follows:

Arndt, C., J. M. Powell, M. J. Aguerre, P. M. Crump, and M. A. Wattiaux. 2015. Journal of Dairy Science 98: 3938-3950.

Benchaar, C., F. Hassanat, R. Gervais, P. Y. Chouinard, H. V. Petit and D. I. Massé. 2014. Methane production, digestion, ruminal fermentation, nitrogen balance, and milk production of cows fed corn silage- or barley silage-based diets. Journal of Dairy Science 97: 961-974.

Brito, A. F. and G. A. Broderick. 2006. Effect of Varying Dietary Ratios of Alfalfa Silage to Corn Silage on Production and Nitrogen Utilization in Lactating Dairy Cows. Journal of Dairy Science 89: 3924-3938.

Broderick, G. A. 2003. Effects of Varying Dietary Protein and Energy Levels on the Production of Lactating Dairy Cows. J. Dairy Sci 86: 1370-1381.

Broderick, G. A. and S. M. Reynal. 2009. Effect of source of rumen-degraded protein on production and ruminal metabolism in lactating dairy cows. Journal of Dairy Science 92: 2822-2834.

Broderick, G. A., A. . Brito and J. J. O. Colmenero. 2007. Effects of feeding formate-treated alfalfa silage or red clover silage on the production of lactating dairy cows. Journal of Dairy Science 90: 1378-1391.

Broderick, G. A., M. J. Stevenson and R. A. Patton. 2009. Effect of dietary protein concentration and degradability on response to rumen-protected methionine in lactating dairy cows. Journal of Dairy Science 92: 2719-2728.

Broderick, G. A., M. J. Stevenson, R. A. Patton, N. E. Lobos and J. J. O. Colmenero. 2008a. Effect of supplementing rumen-protected methionine on production and nitrogen excretion in lactating dairy cows. Journal of Dairy Science 91: 1092-1102.

Broderick, G. A., N. D. Luchini, S. M. Reynal, G. A. Varga and V. A. Ishler. 2008b. Effect on Production of Replacing Dietary Starch with Sucrose in Lactating Dairy Cows. Journal of Dairy Science 91: 4801-4810.

Broderick, G. A., T. M. Kerkman, H. M. Sullivan, M. K. Dowd and P. A. Funk. 2013. Effect of replacing soybean meal protein with protein from upland cottonseed, Pima cottonseed, or extruded Pima cottonseed on production of lactating dairy cows: cottonseed feeding to dairy cows. Journal of Dairy Science 96: 2374-2386.

Cantalapiedra-Hijar, G., J. L. Peyraud, S. Lemosquet, E. Molina-Alcaide, H. Boudra, P. Noziére, et al. 2013. Dietary carbohydrate composition modifies the milk N efficiency in late lactation cows fed low crude protein diets. animal FirstView: 1-11.

Chen, Z. H., G. A. Broderick, N. D. Luchini, B. K. Sloan and E. Devillard. 2011. Effect of feeding different sources of rumen-protected methionine on milk production and N-utilization in lactating dairy cows. Journal of Dairy Science 94: 1978-1988.

Doreau M., A. Ferlay, Y. Rochette, and C. Martin. 2014. Effects of dehydrated lucerne and soya bean meal on milk production and composition, nutrient digestion, and methane and nitrogen losses in dairy cows receiving two different forages. Animal 8(3): 420-430.

Flis, S. A. and M. A. Wattiaux. 2005. Effects of Parity and Supply of Rumen-Degraded and Undegraded Protein on Production and Nitrogen Balance in Holsteins. J. Dairy Sci. 88: 2096-2106.

Gehman, A. M., P. J. Kononoff, C. R. Mullins and B. N. Janicek. 2008.Evaluation of nitrogen utilization and the effects of monensin in dairy cows fed brown midrib corn silage. Journal of Dairy Science 91: 288-300.

Hassanat, F., R. Gervais, C. Julien, D. I. Massé, A. Lettat, P. Y. Chouinard, et al. 2013. Replacing alfalfa silage with corn silage in dairy cow diets: effects on enteric methane production, ruminal fermentation, digestion, n balance, and milk production. J. Dairy Sci. 96: 4553-4567.

Hymes-Fecht, U. C., G. A. Broderick, R. E. Muck and J. H. Grabber. 2013. Replacing alfalfa or red clover silage with birdsfoot trefoil silage in total mixed rations increases production of lactating dairy cows. Journal of Dairy Science 96: 460-469.

Olmos Colmenero, J. J. and G. A. Broderick. 2006a. Effect of Dietary Crude Protein Concentration on Milk Production and Nitrogen Utilization in Lactating Dairy Cows. J. Dairy Sci 89: 1704-1712.

Olmos Colmenero, J. J. and G. A. Broderick. 2006b. Effect of Amount and Ruminal Degradability of Soybean Meal Protein on Performance of Lactating Dairy Cows. J Dairy Sci. 89: 1635-1643.

Reynal, S. M. and G. A. Broderick. 2003. Effects of Feeding Diary Cows Protein Supplements of Varying Ruminal Degradability. Journal of Dairy Science 86: 835-843.

Spek, J. W., J. Dijkstra, G. v. Duinkerken, W. H. Hendriks and A. Bannink 2013. Prediction of urinary nitrogen and urinary urea nitrogen excretion by lactating dairy cattle in northwestern Europe and North America: a meta-analysis. Journal of Dairy Science 96: 4310-4322.

Wattiaux, M. A. and K. L. Karg. 2004. Protein Level for Alfalfa and Corn Silage-Based Diets: II. Nitrogen Balance and Manure Characteristics. J. Dairy Sci. 87: 3492-3502.

Weiss, W. P. and D. J. Wyatt. 2006. Effect of corn silage hybrid and metabolizable protein supply on nitrogen metabolism of lactating dairy cows. Journal of Dairy Science 89: 1644-1653.

The dietary treatments were categorized based on the dietary crude protein (CP). Three treatments had less than or equal to 12.0% CP on a dry matter basis (represented throughout FIGS. 2-5 by a black diamond), three treatments had 12.1-14.4% CP on a dry matter basis (represented throughout FIGS. 2-5 by a grey triangle), twelve treatments had 14.5-15.4% CP on a dry matter basis (represented throughout FIGS. 2-5 by a black square), ten treatments had 15.5-15.9% CP on a dry matter basis (represented throughout FIGS. 2-5 by a grey circle), nine treatments had 16.0-16.4% CP on a dry matter basis (represented throughout FIGS. 2-5 by a black X), seventeen treatments had 16.5-16.9% CP on a dry matter basis (represented throughout FIGS. 2-5 by a grey diamond), fourteen treatments had 17.0-17.4% CP on a dry matter basis (represented throughout FIGS. 2-5 by a black triangle), five treatments had 17.5-17.9% CP on a dry matter basis (represented throughout FIGS. 2-5 by a grey square), and seven treatments had greater than or equal to 18.0% CP on a dry matter basis (represented throughout FIGS. 2-5 by a black circle).

Figure 2:
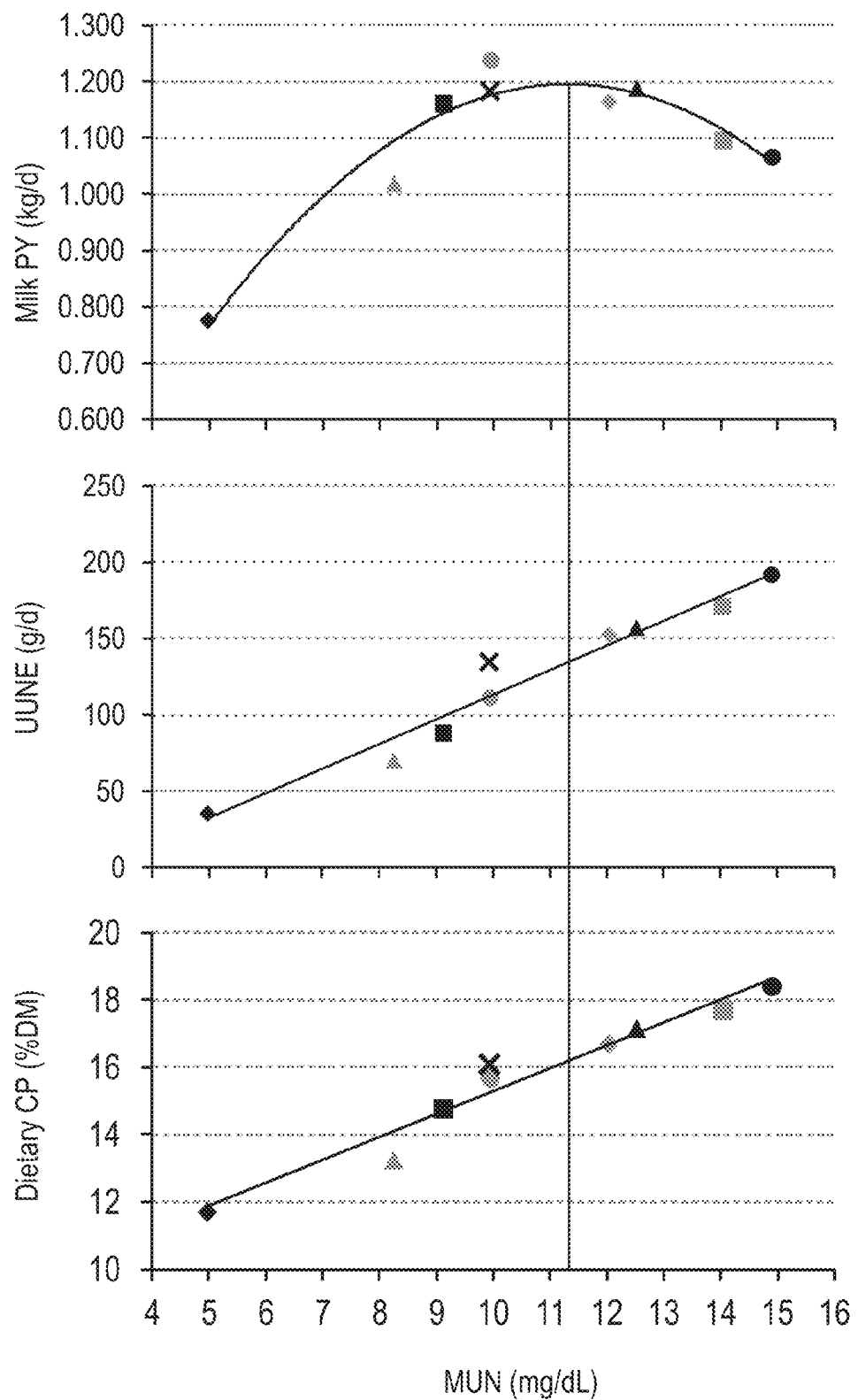
FIG. 2 contains three plots showing the protein yield, the urinary urea-N excretion, and the dietary crude protein versus the milk urea-N, as described in Example 3.

Referring to FIG. 2, the PY, the UUNE, and the dietary CP for each of the aforementioned categories of dietary treatments were each separately plotted versus the MUN. The plotted data were fitted using single (linear) and polynomial (quadratic) regression using Microsoft Excel.

The fit for PY (kg/d) vs. MUN (mg/dL) was described by the following equation:

$$PY=-0.18+0.24MUN-0.01(MUN)^2 \qquad (3)$$

where $r^2=0.93$.

The fit for UUNE (g/d) vs. MUN (mg/dL) was described by the following equation:

$$UUNE=-48.6+16.2MUN \qquad (4)$$

where $r^2=0.95$.

The fit for dietary CP (% dry matter basis) vs. MUN (mg/dL) was described by the following equation:

$$CP=8.47+0.68MUN \qquad (5)$$

where $r^2=0.95$.

Figure 3:
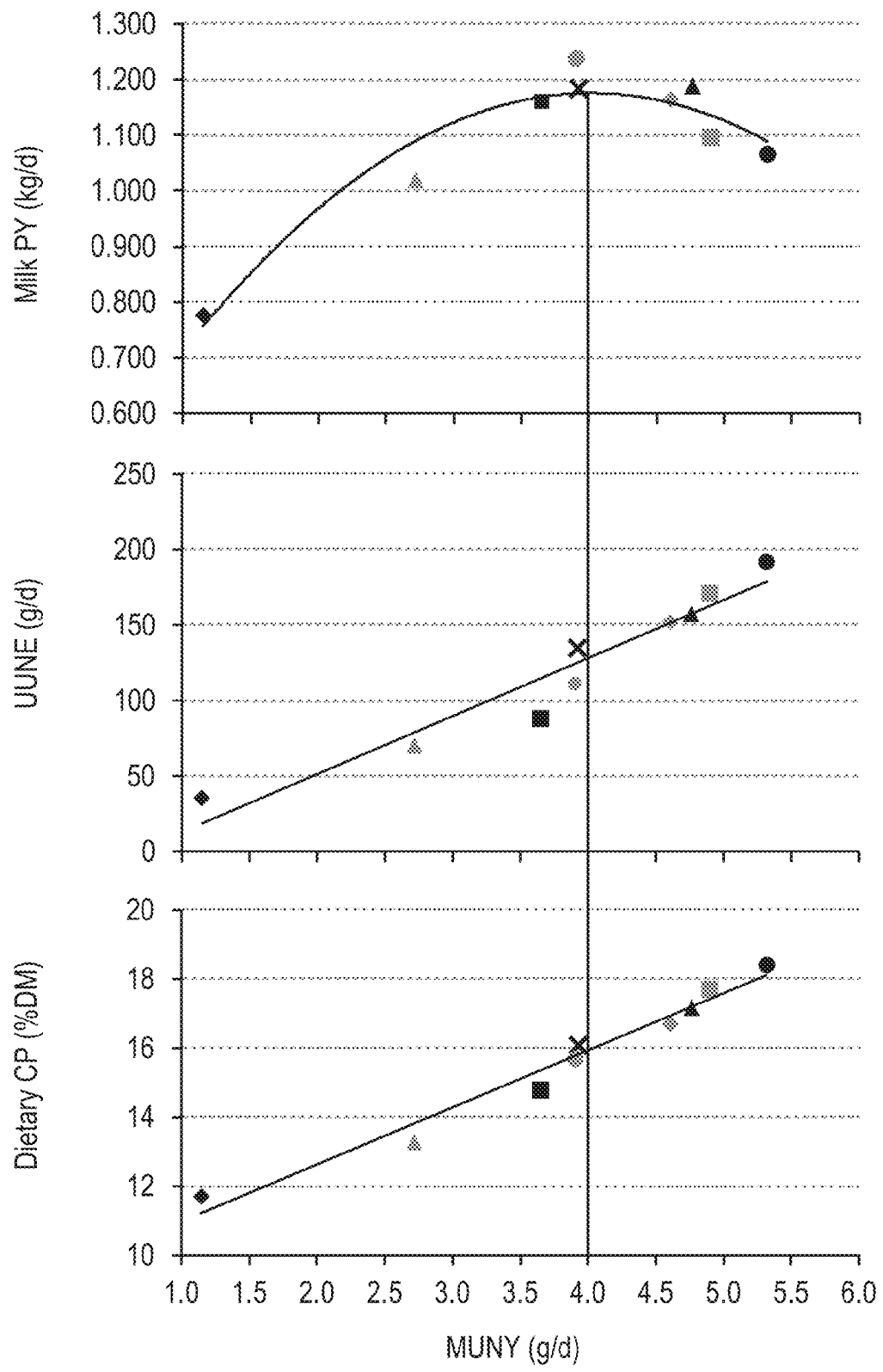
FIG. 3 contains three plots showing the protein yield, the urinary urea-N excretion, and the dietary crude protein versus the milk urea-N yield, as described in Example 3.

Referring to FIG. 3, the PY, the UUNE, and the dietary CP for each of the aforementioned categories of dietary treatments were each separately plotted versus the MUNY. The plotted data were fitted using single (linear) and polynomial (quadratic) regression using Microsoft Excel.

The fit for PY (kg/d) vs. MUNY (g/d) was described by the following equation:

$$PY=-0.35+0.41MUNY-0.05(MUNY)^2 \qquad (6)$$

where $r^2=0.91$.

The fit for UUNE (g/d) vs. MUNY (g/d) was described by the following equation:

$$UUNE=-24.8+38.2MUNY \qquad (7)$$

where $r^2=0.93$.

The fit for dietary CP (% dry matter basis) vs. MUNY (g/d) was described by the following equation:

$$CP=9.32+1.65MUNY \qquad (8)$$

where $r^2=0.96$.

Figure 4:
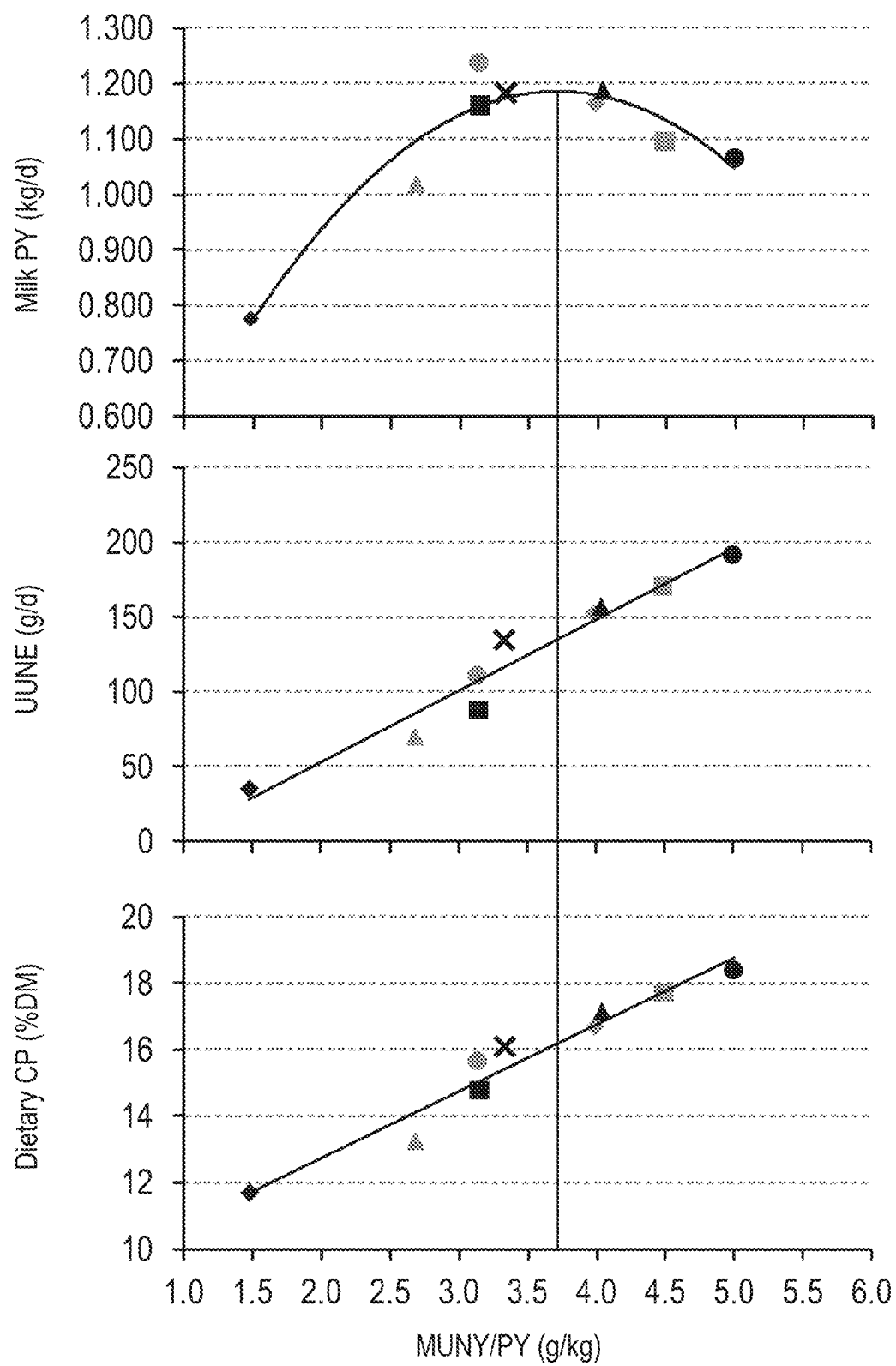
FIG. 4 contains three plots showing the protein yield, the urinary urea-N excretion, and the dietary crude protein versus the ratio of milk urea-N yield to protein yield, as described in Example 3.

Referring to FIG. 4, the PY, the UUNE, and the dietary CP for each of the aforementioned categories of dietary treatments were each separately plotted versus the MUNY/PY ratio. The plotted data were fitted using single (linear) and polynomial (quadratic) regression using Microsoft Excel.

The fit for PY (kg/d) vs. MUNY/PY (g/kg) was described by the following equation:

$$PY=-0.03+0.63(MUNY/PY)-0.08(MUNY/PY)^2 \qquad (9)$$

where $r^2=0.90$.

The fit for UUNE (g/d) vs. MUNY/PY (g/kg) was described by the following equation:

$$UUNE=-41.8+47.6(MUNY/PY) \qquad (10)$$

where $r^2=0.95$.

The fit for dietary CP (% dry matter basis) vs. MUNY/PY (g/kg) was described by the following equation:

$$CP=8.74+2.01(MUNY/PY) \qquad (11)$$

where $r^2=0.95$.

Figure 5:
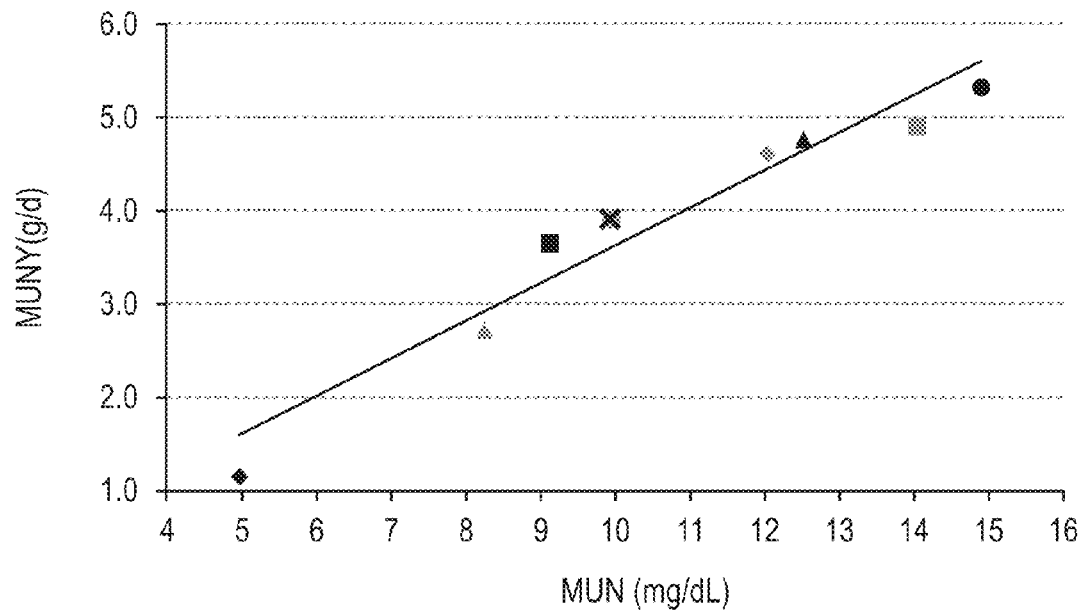
FIG. 5 contains two plots showing the milk urea-N yield and the ratio of the milk urea-N yield to protein yield versus the milk urea-N, as described in Example 3.
Figure 5:
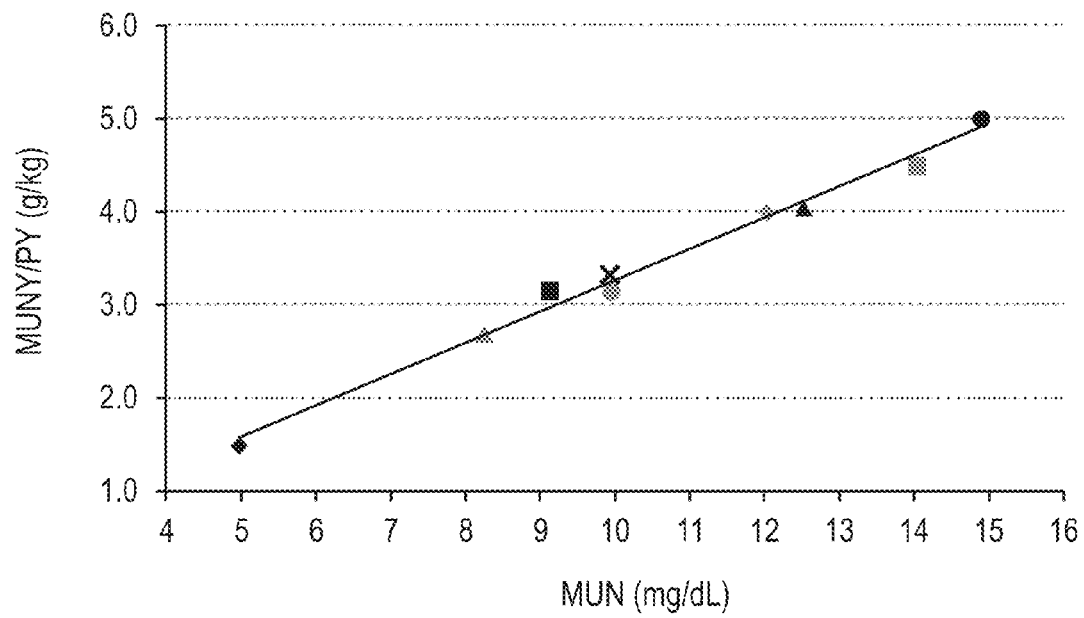

Referring to FIG. 5, MUNY and MUNY/PY for each of the aforementioned categories of dietary treatments were each separately plotted versus the MUN. The plotted data were fitted using single (linear) and polynomial (quadratic) regression using Microsoft Excel.

The fit for MUNY (g/d) vs. MUN (mg/dL) was described by the following equation:

$$MUNY=-0.42+0.40MUN \qquad (12)$$

where $r^2=0.94$.

The fit for MUNY/PY (g/kg) vs. MUN (mg/dL) was described by the following equation:

$$(MUNY/PY)=-0.11+0.34MUN \qquad (13)$$

where $r^2=0.98$.

The relationships suggested that there is an optimum MUNY (FIG. 3) and (or) MUN/PY (FIG. 4) that maximizes milk protein yield (the desired product) while minimizing urinary urea-N excretion (the undesirable product). To the right of the vertical bar in each Figure, dietary CP was likely higher than desirable. The animal consumed excess dietary CP, urinary urea-N was elevated, and milk protein yield was not greater compared with the optimal level of CP in the diet. To the left of the vertical bar in each Figure, dietary CP was likely lower than desirable. The animal consumed inadequate amount of dietary CP, urinary urea-N was reduced, and milk protein yield was decreasing rapidly compared with the optimal level of CP in the diet.

Example 4

Five different methods of calculating the ratio of PY/MUNY were utilized in the following example. Data were collected by sampling two consecutive milkings (pm and am) in week 12 of a study with 122 Holstein cows (mean±SD: 303±55 DIM; 761±77 kg BW) fed a 16.2, 14.4, 13.1 or 11.8% CP (DM basis) TMR for 12 weeks. The following methods of calculation were used: A) daily PY divided by daily MUNY, where daily values were calculated using six DHIA values (milk production, milk protein %, and MUN for each of the pm and am sampling); B) milk protein % divided by MUN (averages of pm and am for both); C) milk protein % divided by MUN using am values only; D) milk protein % divided by MUN using pm values only; and E) an average of methods C and D. Ratios were analyzed in SAS 9.3 with PROC MIXED and single df orthogonal contrasts in order to compare methods B, C, D, and E to method A. The values computed by methods A, B, and E were comparable, whereas the values computed by methods C and D were not comparable to the others. Method C overestimated and method D underestimated the PY/MUNY ratio relative to the other methods. The calculated values and corresponding contrast p-values (comparing methods B, C, D, and E to method A) are shown below in Table 1.

TABLE 1

| Dietary CP | Method | | | | | Contrast P-value | | | |
|---|---|---|---|---|---|---|---|---|---|
| | A | B | C | D | E | A vs B | A vs C | A vs D | A vs E |
| 16.2% DM | 291 | 289 | 309 | 274 | 291 | 0.906 | 0.222 | 0.239 | 0.982 |
| 14.4% DM | 333 | 329 | 364 | 304 | 334 | 0.838 | 0.119 | 0.150 | 0.946 |
| 13.1% DM | 494 | 480 | 627 | 397 | 512 | 0.760 | 0.009 | 0.043 | 0.686 |
| 11.8% DM | 763 | 744 | 1042 | 647 | 844 | 0.884 | 0.048 | 0.383 | 0.536 |
| Overall | 470 | 461 | 585 | 405 | 495 | 0.596 | <.001 | <.001 | 0.164 |

Other aspects and uses of the invention will be apparent to those skilled in the art from consideration from the specification and practice of the invention disclosed herein. All references cited herein for any reason, including all journal citations and U.S./foreign patents and patent applications, are specifically and entirely incorporated herein by reference. It is understood that the invention is not confined to the specific reagents, formulations, reaction conditions, etc., herein illustrated and described, but embraces such modified forms thereof as come within the scope of the following claims.

What is claimed is:

1. A method for feeding a herd of interest of milk-producing animals, the method comprising:
    a) measuring from a herd of milk-producing animals to produce an observation data set comprising an amount of milk produced by the herd of interest on an observation date ($MP_O$), a concentration of urea-N in milk produced by the herd of interest on the observation date ($MUN_O$), a protein yield in milk produced by the herd of interest on the observation date ($PY_O$), and a percent dietary crude protein in feedstock consumed by the herd of interest on the observation date or a date one to seven days before the observation date ($CP_O$) on a dry matter basis;
    b) calculating a ratio ($MUNY_O/PY_O$) of a milk urea-N yield by the herd of interest on the observation date ($MUNY_O$) to the $PY_O$, wherein the $MUNY_O$ is the $MUN_O$ divided by the $MP_O$;
    c) defining an optimal target ratio ($MUNY_T/PY_T$);
    d) generating a report indicating use of a first feedstock if the $MUNY_O/PY_O$ is less than the $MUNY_T/PY_T$ or indicating use of a second feedstock if the $MUNY_O/PY_O$ is greater than the $MUNY_T/PY_T$, wherein the first and second feedstocks differ from one another; and
    e) feeding the herd of interest on one or more days after the observation date with the first or second feedstock indicated by the report.

2. The method of claim 1, the method further comprising:
    repeating steps a), b), and d) substituting a new observation date for the observation date, wherein the new observation date is one or more days after the observation date.

3. The method of claim 1, the method further comprising:
    accessibly storing a historical data set comprising an amount of milk produced by the herd of interest, one or more comparable herds, or a combination thereof on one or more dates within a historical time window ($MP_H$), a concentration of urea-N in milk produced by the herd of interest, the one or more comparable herds, or a combination thereof on the one or more dates within the historical time window ($MUN_H$), a protein yield in milk produced by the herd of interest, the one or more comparable herds, or a combination thereof on the one or more dates within the historical time window ($PY_H$), and a percent dietary crude protein in feedstock consumed by the herd of interest, the one or more comparable herds, or a combination thereof on the one or more dates or a date one to seven days before the one or more dates within the historical time window ($CP_H$) on a dry matter basis; and
    using the historical data set in step c).

4. The method of claim 3, wherein step c) comprises a regression analysis of the historical data set.

5. The method of claim 3, the method further comprising:
    adding the observation data set to the historical data set and including the observation date in the historical time window; and
    repeating steps a), b), and d) substituting a new observation date for the observation date, wherein the new observation date is one or more days after the observation date.

6. The method of claim 1, wherein the $PY_O$ is between about 500 grams per day and about 2000 grams per day.

7. The method of claim 1, wherein the $MUNY_O$ is between about 1.0 grams per day and about 10.0 grams per day.

8. The method of claim 1, wherein the milk-producing animals are dairy cattle.

9. The method of claim 1, the method further comprising:
    measuring the $MP_O$, the $MUN_O$, the $PY_O$, and the $CP_O$ to form the observation data set.

10. The method of claim 1, wherein the method does not directly measure any properties of the urine of the herd of interest of milk-producing animals.

* * * * *